United States Patent [19]

Karrer

[11] Patent Number: 4,569,997
[45] Date of Patent: Feb. 11, 1986

[54] POLYALKYLPIPERIDINE COMPOUNDS

[75] Inventor: Friedrich Karrer, Zofingen, Switzerland

[73] Assignee: Ciba Geigy Corporation, Ardsley, N.Y.

[21] Appl. No.: 537,134

[22] Filed: Sep. 29, 1983

[30] Foreign Application Priority Data

Aug. 10, 1982 [CH] Switzerland ............ 5924/82

[51] Int. Cl.$^4$ .......................... C07D 491/10
[52] U.S. Cl. ...................... 546/19; 546/23; 546/187; 546/188; 546/189; 544/98; 544/99; 544/100; 544/103
[58] Field of Search ............ 546/189, 188, 187, 19, 546/23; 260/239.3 R

[56] References Cited

U.S. PATENT DOCUMENTS

| 3,527,762 | 9/1970 | Jack et al. | 546/189 |
| 3,940,363 | 2/1976 | Murayama et al. | 546/189 |
| 4,021,432 | 5/1977 | Holt et al. | 546/189 |
| 4,247,449 | 1/1981 | Wieser et al. | 546/19 |

Primary Examiner—Robert T. Bond
Attorney, Agent, or Firm—Harry Falber

[57] ABSTRACT

By reacting compounds of the formula

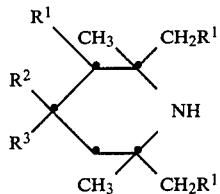

with diisocyanates or triisocyanates of the formula $R^4(NCO)_n$ at a low temperature, the corresponding 1-carbamyl compounds of the formula I

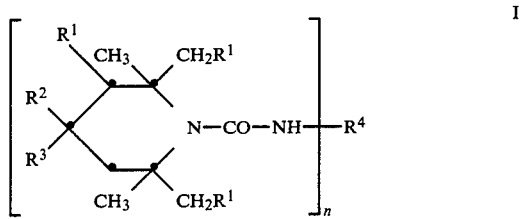

in which n is 2 or 3 and $R^1$, $R^2$, $R^3$ and $R^4$ are as defined in claim 1, are obtained. The compounds of the formula 1 are light stabilizers for organic materials, especially for varnishes.

4 Claims, No Drawings

POLYALKYLPIPERIDINE COMPOUNDS

The present invention relates to novel polyalkylpiperidine compounds, a process for their preparation and plastics stabilised with these compounds.

Piperidines which are alkylated in the 2- and 6-position belong to the class of sterically hindered amines which can be used as stabilisers for light-sensitive organic materials. Such piperidine compounds usually have a polar group in the 4-position and can be unsubstituted in the 1-position or substituted by monovalent radicals. German Offenlegungsschrift No. 2,338,076 also describes bis-piperidine compounds in which two 2,2,6,6-tetramethylpiperidines substituted in the 4-position are linked to one another in the 1-position by divalent radicals. The divalent radicals used for this are, in particular, alkylene radicals, alkylene radicals which are interrupted by ether, ester or thioether groups and aliphatic dicarboxylic acid radicals.

Compared with monopiperidine derivatives, such bis-piperidine derivatives generally have the advantage of being less volatile and being extractable. It would therefore also be of interest to achieve such an enlargement of the molecule by reaction of polyalkylpiperidines which are unsubstituted in the 1-position with diisocyanates (or trisiocyanates). However, it is known that the sterically hindered piperidines undergo carbamylation in the 1-position only with very great difficulty. Thus, in Example 87 of German Offenlegungsschrift No. 2,258,752, only an 80% pure product is obtained in the reaction of 2,2,6,6-tetramethylpiperidin-4-ol with excess methyl isocyanate in boiling benzene for 24 hours, whilst according to Example 45 of the same publication, the reaction of 1-substituted tetramethylpiperidin-4-ols with methyl isocyanate proceeds without difficulty. From this, it was possible to conclude that carbamylation of the sterically hindered piperidine nitrogen proceeds only very slowly and incompletely, so that there is no chance of obtaining pure bis-piperidine compounds by reaction with diisocyanates.

German Offenlegungsschrift No. 2,834,455 describes the reaction of 4-spiro-oxazolone-polyalkylpiperidines with diisocyanates, reaction taking place only on the oxazolidone nitrogen and not on the piperidine nitrogen:

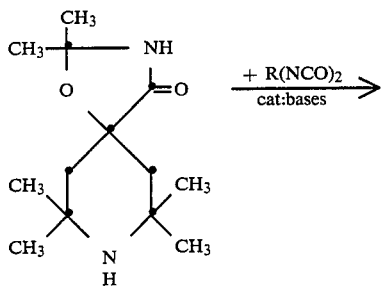

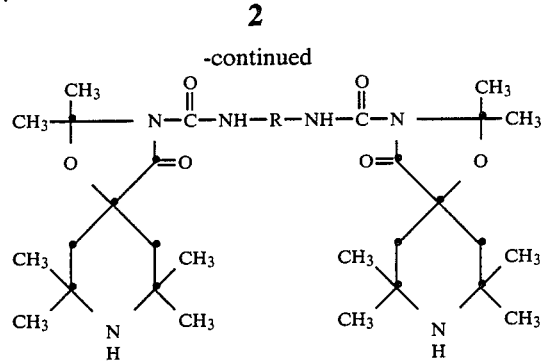

No noticeable amounts of 1-carbamyl products are thus obtained under the reaction conditions described therein (15 hours in boiling toluene).

It was therefore surprising to discover that virtually the quantitative amount of the corresponding bis- or tris-1-carbamylpiperidines are formed within a short time when 1-unsubstituted polyalkyl-piperidine derivatives are reacted with diisocyanates or triisocyanates at room temperature. Against all expectations, 1-carbamylation, which under the influence of heat does not proceed at all or proceeds only incompletely, thus proceeds rapidly and with a high yield in the cold. Such bis- and tris-1-carbamylpiperidines have become accessible for the first time by this preparation process.

The present invention thus relates to compounds of the formula I

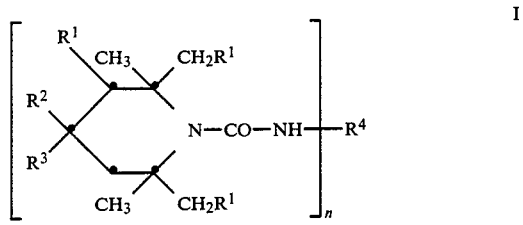

in which n is 2 or 3, $R^1$ is hydrogen or $C_1$-$C_4$-alkyl, $R^2$ is hydrogen, —OH, —$OR^5$, —$COOR^6$, —$CH_2COOR^6$, —$CH_2CN$, —CN, —$N(R^7)_2$, —CO—$N(R^{7a})_2$, —$CH_2CH_2N(R^7)_2$, —$N(R^{7a})$—CO—$R^8$, —O—CO—$R^9$, —$OCH_2CH_2$—CN, —$N(R^{7a})$—CO—O—$R^{10}$, —O—CO—O—$R^{10}$, —O—CO—$N(R^{7a})_2$ or a group

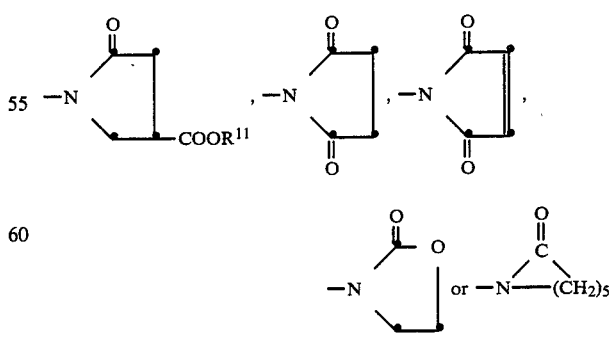

and $R^3$ is hydrogen, or $R^2$ and $R^3$ together are O=, NC—CH= or a group of the formula II, III, IV, V or VI

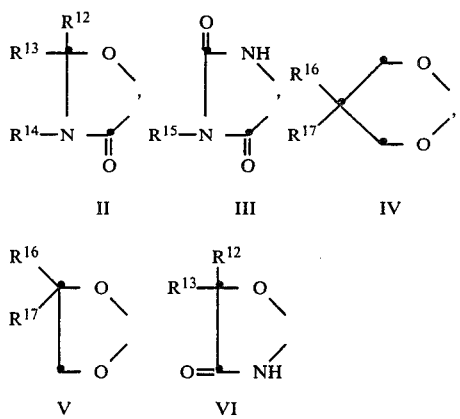

II  III  IV

V  VI $R^4$ is an n-valent radical of an aliphatic, cycloaliphatic, aromatic or aromatic-aliphatic diisocyanate or triisocyanate, $R^5$ is $C_1$–$C_{12}$-alkyl, $C_3$–$C_{14}$-oxaalkyl, $C_3$–$C_5$-alkenyl, propargyl, benzyl or —$(CH_2CH_2O)_pH$ where p is 1–10, $R^6$ is hydrogen, $C_1$–$C_{18}$-alkyl, $C_3$–$C_5$-alkenyl, $C_5$–$C_8$-cycloalkyl, $C_6$–$C_{10}$-aryl, $C_7$–$C_{12}$-alkylaryl, $C_7$–$C_{12}$-phenylalkyl or a group of the formula VI

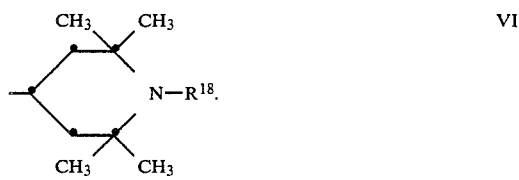

VI $R^7$ is $C_1$–$C_{18}$-alkyl, $C_2$–$C_{14}$-oxaalkyl, $C_3$–$C_5$-alkenyl, $C_5$–$C_8$-cycloalkyl, $C_7$–$C_{12}$-phenylalkyl, $C_6$–$C_{10}$-aryl, $C_2$–$C_4$-hydroxyalkyl or $C_7$–$C_{10}$-cycloalkyl-alkyl, or the two radicals $R^7$, together with the N atom to which they are bonded, are a 5- to 7-membered ring, $R^{7a}$ is hydrogen or has one of the meanings of $R^7$, $R^8$ is $C_1$–$C_{12}$-alkyl, $C_3$–$C_{14}$-oxaalkyl, $C_2$–$C_{14}$-alkyl which is substituted by —COOH or —COO($C_1$–$C_4$-alkyl), or $C_2$–$C_5$-alkenyl, $C_5$–$C_8$-cycloalkyl, $C_7$–$C_{12}$-phenylalkyl, $C_6$–$C_{10}$-aryl or $C_7$–$C_{12}$-alkylaryl, $R^9$ is $C_1$–$C_{18}$-alkyl, $C_3$–$C_{14}$-oxaalkyl, $C_2$–$C_{14}$-alkyl which is substituted by —COOH or —COO($C_1$–$C_4$-alkyl), or $C_2$–$C_5$-alkenyl, $C_5$–$C_8$-cycloalkyl, $C_6$–$C_{10}$-aryl, $C_7$–$C_{12}$-phenylalkyl, $C_7$–$C_{12}$-alkylaryl or phenyl or $C_7$–$C_{10}$-phenylalkyl which is substituted by OH and 1–3 $C_1$–$C_4$-alkyl groups, $R^{10}$ is $C_1$–$C_{12}$-alkyl, $C_3$–$C_5$-alkenyl, $C_5$–$C_8$ cycloalkyl, phenyl or $C_7$–$C_{12}$-phenylalkyl, $R^{11}$ is hydrogen or $C_1$–$C_8$-alkyl, $R^{12}$ is hydrogen, $C_1$–$C_{12}$-alkyl, $C_5$–$C_8$-cycloalkyl or benzyl and $R^{13}$ is $C_1$–$C_{12}$-alkyl, $C_5$–$C_8$-cycloalkyl or phenyl, or $R^{12}$ and $R^{13}$, together with the C atom to which they are bonded, are a $C_6$–$C_{14}$-cycloalkane or alkylcycloalkane ring, $R^{14}$ is hydrogen, $C_1$–$C_{12}$-alkyl, $C_3$–$C_5$-alkenyl, $C_5$–$C_8$-cycloalkyl, $C_2$–$C_4$-hydroxyalkyl, $C_2$–$C_{10}$-alkanoyl, benzoyl, $C_7$–$C_{12}$-phenylalkyl or a group R—NH—CO—, in which R is $C_1$–$C_8$-alkyl or phenyl, $R^{15}$ is hydrogen, $C_1$–$C_{18}$-alkyl, $C_3$–$C_5$-alkenyl, $C_2$–$C_4$-hydroxyalkyl, $C_5$–$C_8$-cycloalkyl, $C_7$–$C_{12}$-phenylalkyl or glycidyl, $R^{16}$ is hydrogen or $C_1$–$C_4$-alkyl, $R^{17}$ is hydrogen, methyl, ethyl or hydroxymethyl and $R^{18}$ is hydrogen, $C_1$–$C_4$-alkyl, allyl, benzyl, acetyl or acryloyl.

The substituents $R^1$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{18}$ in formula I can be alkyl, and can thereby be a straight-chain or branched alkyl radical.

Examples of such alkyl radicals—within the number of C-atoms defined—are methyl, ethyl, n-propyl, isopropyl, sec.-butyl, n-butyl, tert.-butyl, isoamyl, n-hexyl, 2-ethylbutyl, isoheptyl, n-octyl, 2-ethylhexyl, n-nonyl, isodecyl, 3,3,5,5-tetramethylhexyl, n-dodecyl, n-tetradecyl, n-hexadecyl and n-octadecyl.

Possible examples of hydroxyalkyl $R^7$, $R^{14}$ and $R^{15}$ are 2-hydroxyethyl, 2-hydroxypropyl, 3-hydroxypropyl and 2-hydroxybutyl. Oxaalkyl $R^5$, $R^6$, $R^8$ and $R^9$ can be monooxaalkyl or polyoxaalkyl, for example 2-ethoxyethyl, 2-isopropoxyethyl, butoxymethyl, 2-hexyloxyethyl, 3,6-dioxaheptyl, 3,6-dioxadecyl, 3,6,9-trioxadecyl or 3-dodecyloxypropyl. Oxaalkyl $R^7$ can moreover also be methoxymethyl.

Possible examples of $C_2$–$C_{14}$-alkyl $R^8$ and $R^9$ which is substituted by —COOH or —COO($C_1$–$C_4$-alkyl) are 2-carboxyethyl, 2-methoxycarbonyl-butyl, 2-ethoxycarbonyldecyl, 2-carboxy-tetradecyl and 2-isopropoxycarbonyl-tetradecyl.

Possible examples of alkenyl $R^5$, $R^7$, $R^{10}$, $R^{14}$ and $R^{15}$ are methallyl, 2-butenyl and 2-methyl-2-butenyl, but preferably allyl. Alkenyl $R^8$ and $R^9$ can also be vinyl, 1-methylvinyl and 2-methylvinyl.

$R^6$, $R^7$, $R^8$, $R^9$, $R^{10}$, $R^{12}$, $R^{13}$, $R^{14}$, and $R^{15}$ can be cycloalkyl, for example cyclopentyl, cyclohexyl, cycloheptyl or cyclooctyl. Possible examples of cycloalkylalkyl $R^7$ are cyclohexylmethyl, cyclopentylethyl and 3-cyclohexylpropyl.

Aryl $R^6$, $R^7$, $R^8$ and $R^9$ can be phenyl or naphthyl. Possible examples of phenyl or phenylalkyl $R^9$ which is substituted by OH and alkyl are 4-hydroxy-3,5-ditert.-butylphenyl, 4-hydroxy-3-methyl-5-tert.-butylbenzyl, 3-hydroxy-4-tert.-butylbenzyl and 2-(4-hydroxy-3,5-ditert.-butylphenyl)-ethyl or -propyl.

Possible examples of $C_7$–$C_{12}$-alkylaryl $R^6$, $R^8$ and $R^7$ are tolyl xylyl, 4-tert.-butylphenyl, 4-methyl-1-naphthyl and 3-ethylphenyl. Possible examples of phenylalkyl $R^6$, $R^7$, $R^8$, $R^9$, $R^{10}$, $R^{14}$ and $R^{15}$ are benzyl, 2-phenylethyl, 2-phenylpropyl, 3-phenylpropyl, 4-phenylbutyl and 4-methylbenzyl.

Possible examples of $C_2$–$C_{10}$-alkanoyl $R^{14}$ are acetyl, propionyl, butyryl, hexanoyl, α,α-dimethylpropionyl, octanoyl and decanoyl. If the group $N(R^7)_2$ is a 5- to 7-membered ring, this can be, for example, a pyrrolidine, piperidine, morpholine or 4-alkylpiperazine ring.

If $R^{12}$ and $R^{13}$ together with the connecting C atom form a cycloalkane or alkylcycloalkane ring, this can be, for example, a cyclopentane, cyclohexane, mono- or di-methylcyclohexane, ethylcyclopentane, cyclooctane or cyclododecane ring.

Possible examples of a divalent radical $R^4$ of an aliphatic diisocyanate are di-, tri-, tetra-, hexa-, octadeca- and dodeca-methylene. Possible examples of a radical $R^4$ of a cycloaliphatic diisocyanate are 1,4-cyclohexylene, 4-methyl-1,3-cyclohexylene, the radical

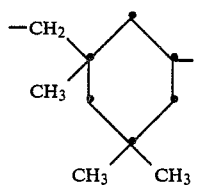

and a radical of the formula

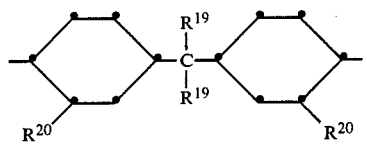

in which $R^{19}$ is H, $CH_3$ or $C_2H_5$ and $R^{20}$ is H or $CH_3$. Possible examples of a radical $R^4$ of an aromatic or aromatic-aliphatic diisocyanate are 1,4-phenylene, 1,3-phenylene, 2,4-tolylene, 2,6-tolylene, 1,4-naphthylene, 1,5-naphthylene, 4,4'-diphenylene and a radical of the formula

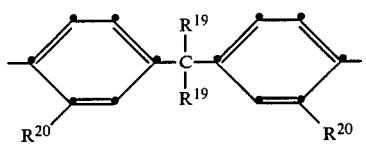

A trivalent radical $R^4$ of a triisocyanate can be aliphatic, cycloaliphatic or aromatic-aliphatic. Examples are the radicals of the formulae

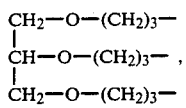

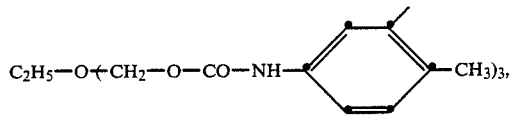

and

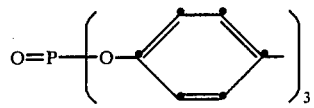

If n is 2, $R^4$ is preferably a divalent saturated aliphatic radical having 2-16 C atoms, a divalent cycloaliphatic radical having 5-20 C atoms or a divalent aromatic or aromatic-aliphatic radical having 6-20 C atoms, and if n is 3, $R^4$ is preferably a trivalent aromatic-aliphatic radical having 10-30 C atoms.

The preferred compounds of the formula I are those in which $R^1$ is hydrogen, which are derivatives of 2,2,6,6-tetramethylpiperidine.

Other preferred compounds of the formula 1 are those in which $R^1$ is hydrogen, $R^2$ is —OH, —OR$^5$, —CH$_2$COOR$^6$, —CH$_2$CN, —N(R$^7$)—CO—R$^8$, —O—CO—R$^9$, —N(R$^7$)—CO—OR$^{10}$ or —O—CO—N(R$^7$)$_2$ and $R^3$ is hydrogen, or $R^2$ and $R^3$ together are O= or a group of the formula II, III, IV or V, and, if n is 2, $R^4$ is $C_2$-$C_{12}$-alkylene, phenylene, naphthylene, tolylene or a group of the formula

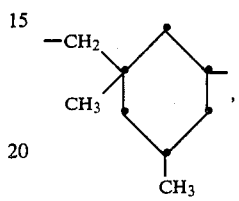

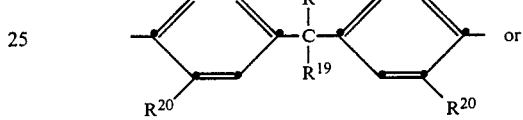

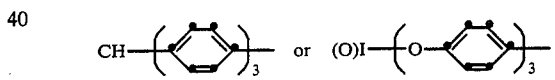

in which $R^{19}$ is hydrogen, methyl or ethyl and $R^{20}$ is hydrogen or methyl, and, if n is 3, $R^4$ is a group of the formula

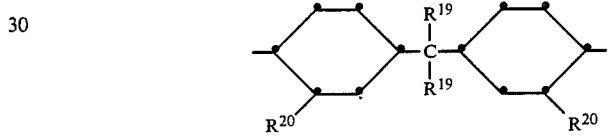

$R^5$ is $C_1$-$C_{12}$-alkyl, $C_3$-$C_5$-alkenyl or benzyl, $R^6$ is $C_1$-$C_4$-alkyl or cyclohexyl, $R^7$ is $C_1$-$C_{12}$-alkyl, cyclohexyl, allyl or phenyl, $R^8$ and $R^9$ are $C_1$-$C_{12}$-alkyl, $C_2$-$C_3$-alkenyl, phenyl, benzyl or cyclohexyl and $R^{10}$ is $C_1$-$C_{12}$-alkyl or phenyl.

Examples of specific compounds of the formula I are those of the following formulae:

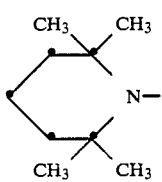N—CO—NH—(CH$_2$)$_6$—NH—CO—N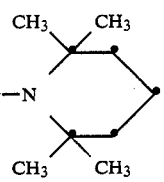

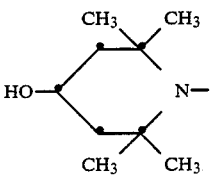N—CO—NH—⬡—NH—CO—N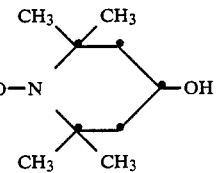

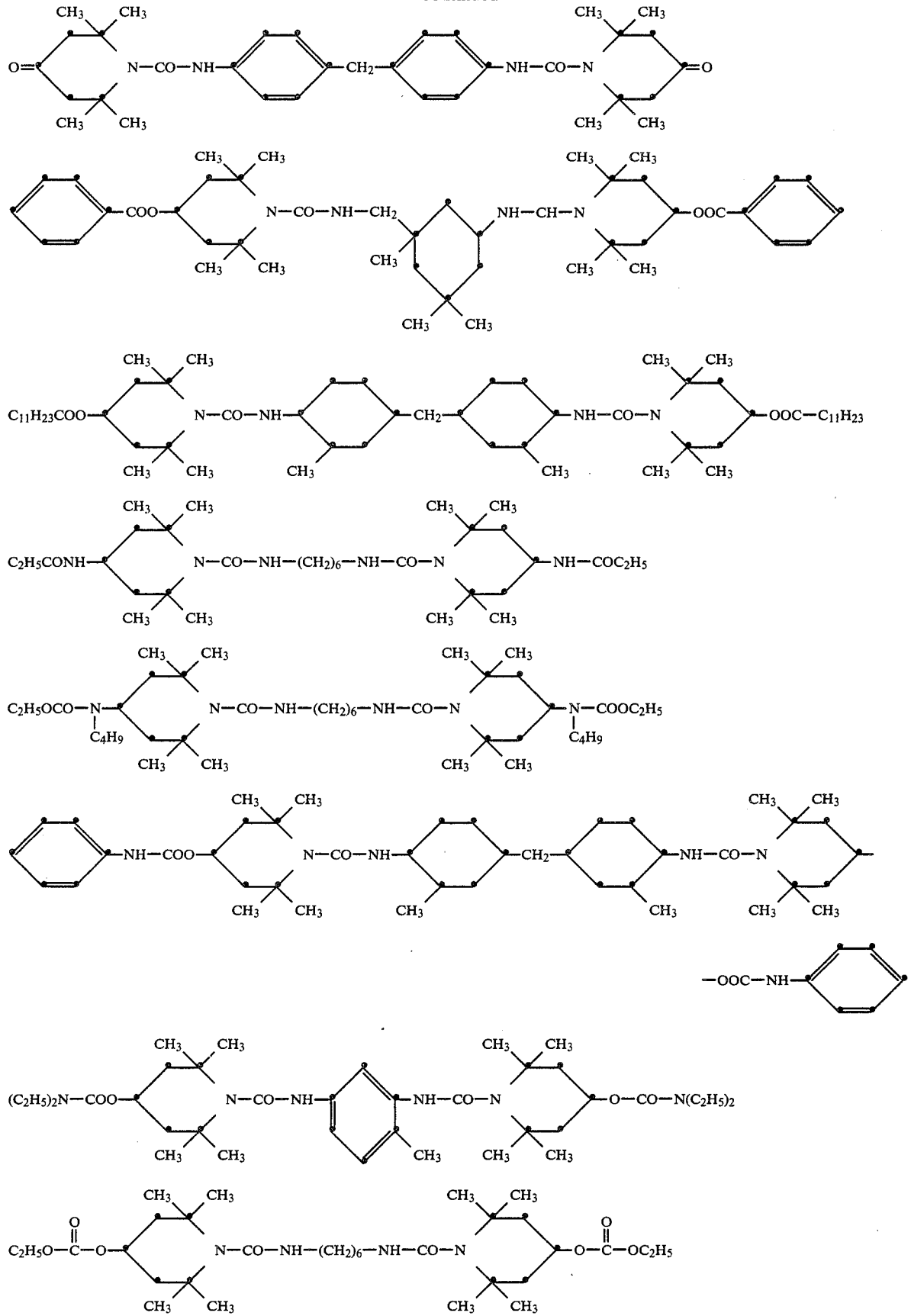

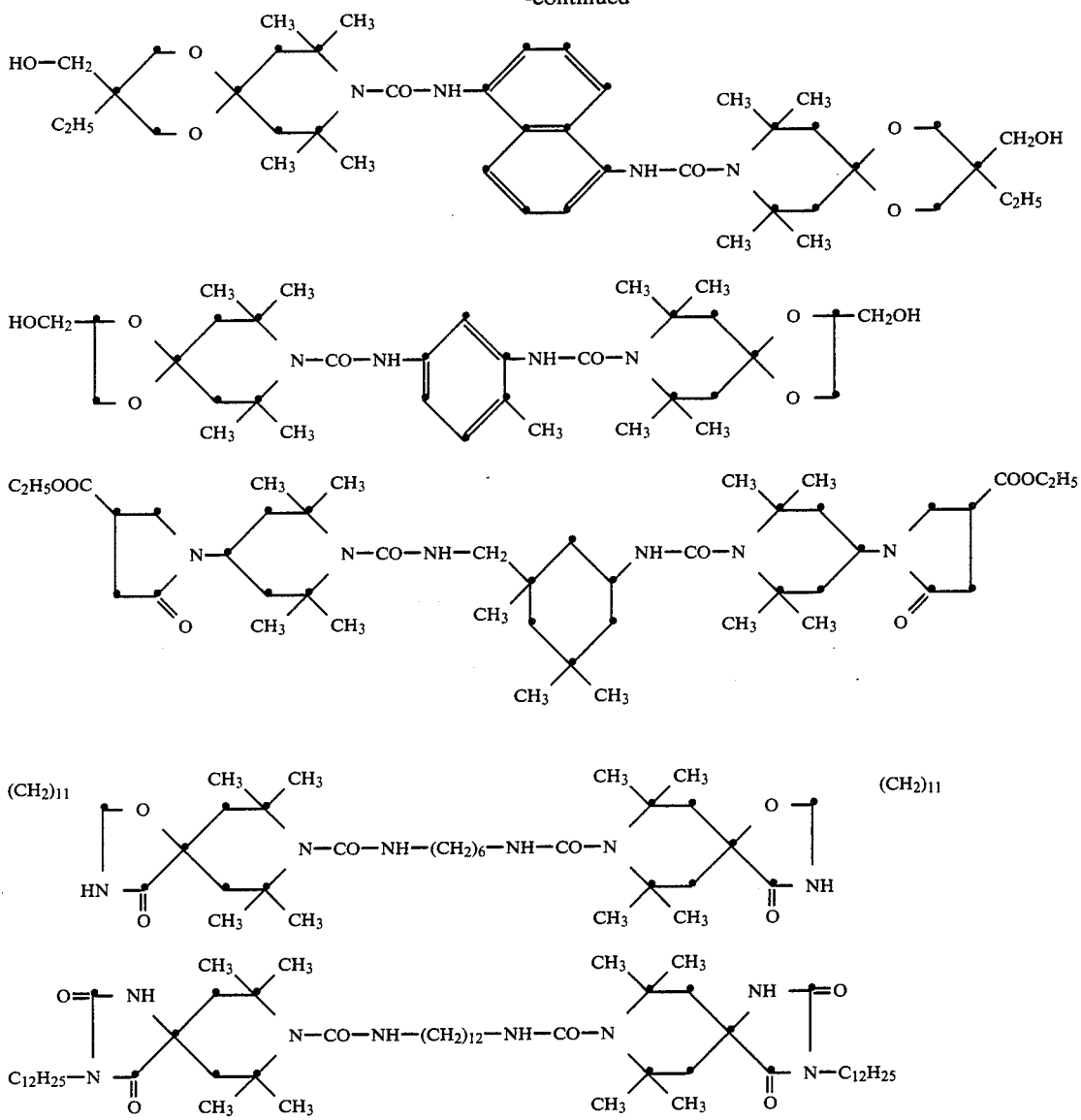

As mentioned above, the compounds of the formula I can be prepared in a high yield and high purity by carbamylation of the corresponding polyalkylpiperidines which are unsubstituted in the 1-position, at a relatively low temperature. The invention thus also relates to a process for the preparation of compounds of the formula I by reacting compounds of the formula VII

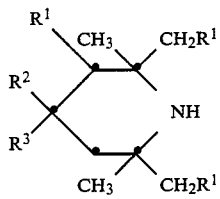

VII with diisocyanates or triisocyanates of the formula VIII

VIII in a molar ratio of n mols of VII to 1 mol of VIII in an inert solvent, which comprises carrying out the reaction at −20° C. to +50° C., preferably at −5° C. to +30° C.

Particularly suitable inert solvents are hydrocarbons, such as pentane, hexane, heptane, ligroin, benzine, cyclohexane, benzene, toluene and xylene, and ethers, for example diethyl ether, diisopropyl ether, tetrahydrofuran, dioxane and 1,2-dimethoxyethane.

Advantageously, a solution of the compound VII is taken, and a solution of the compound VIII is added, while stirring and cooling. The temperature of the reaction mixture should thereby be kept below 50° C., preferably below 30° C.

2 Moles of the compound VII are used per mole of diisocyanate, and 3 moles of the compound VII are used per mole of triisocyanate. The reaction can be accelerated by adding catalytic amounts of bases soluble in organic solvents. Examples are 1,4-diazabicyclo[2,2,-2]octane and 1,8-diazabicyclo[5.4.0]undec-7-ene. However, such a catalyst is not necessary.

The products formed precipitate directly in crystalline form from the reaction solution, or they can be made to crystallise by cooling, or some or all of the solvent is first distilled off and the product is then allowed to crystallise in the cold. The products are thus obtained in high purity. Even if there is a possibility of the formation of by-products, a high yield of the desired 1-carbamyl compound is formed at low temperatures, which demonstrates the surprising selectivity of the process. For example, if diisocyanates are reacted with 2 moles of 4-hydroxy-2,2,6,6-tetramethylpiperidine at room temperature (20°–25° C.) according to the present process, the 1-carbamyl compounds of the formula

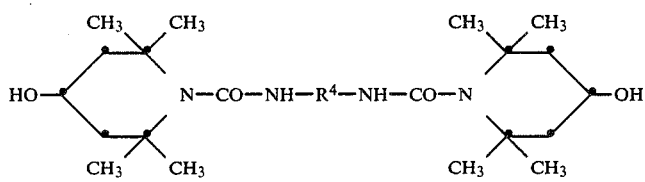

are formed in high yield, whilst the 4-carbamyloxy compounds

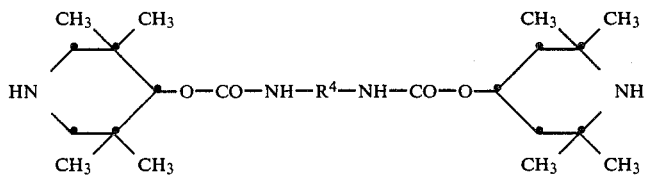

are chiefly formed in the known procedure under the influence of heat (reflux, toluene).

The compounds of the formula I can be used as stabilisers for light-sensitive organic materials, for example for cosmetics or coatings for colour photography, but especially for organic polymers. In addition to a pronounced light-stabilising action, the compounds of the formula I also have a certain stabilising action towards heat and oxidated ageing of the polymer. Examples of such polymers are as follows:

1. Polymers of mono and diolefins, for example polyethylene (which may be crosslinked or non-crosslinked), polypropylenes, polyisobutylenes, polybut-1-ene, polymethylpent-1-ene, polyisoprene and polybutydiene, and polymers of cycloolefins, for example of cyclopentane or norbornene.

2. Mixtures of the polymers mentioned under (1), for example mixtures of polypropylene with polyethylene or with polyisobutylene.

3. Copolymers of monoolefins and diolefins with one another or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkylacrylate copolymers, ethylene/alkyl methacrylate copolymers, ethylene/vinyl acetate copolymers and ethylene/acrylic acid copolymers and salts thereof (ionomers), and terpolymers of ethylene with propylene and a diene, such as hexadiene, dicyclopentadiene or ethylidenenorbornene.

4. Polystyrene.

5. Copolymers of styrene or α-methylstyrene with dienes or acrylic derivatives, for example styrene/butadiene, styrene/acrylonitrile, styrene/ethyl methacrylate, styrene/butadiene/ethyl acrylate and styrene/acrylonitrile/methyl acrylate; high impact mixtures of styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

6. Graft copolymers of styrene, for example styrene on polybutadiene, styrene and acrylonitrile on polybutadiene, styrene and maleic anhydride on polybutadiene, styrene and alkylacrylates or alkylmethacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under (5), for example those known as so-called ABS, MBS, ASA or AES polymers.

7. Halogen-containing polymers, for example polychloroprene, chlorinated rubber, chlorinated or chlorosulfonated polyethylene and epichlorohydrin homopolymers and copolymers, and in particular polymers of halogen-containing vinyl compounds, for example polyvinyl chloride, polyvinylidene chloride, polyvinyl fluoride and polyvinylidene fluoride; and copolymers thereof, such as vinyl chloride/vinylidene chloride, vinyl chloride/vinyl acetate and vinylidene chloride/vinyl acetate.

8. Polymers which are derived from $\alpha,\beta$-unsaturated acids and derivatives thereof, such as polyacrylates, polymethacrylates, polyacrylamides and polyacrylonitriles.

9. Copolymers of the monomers mentioned under (8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers and acrylonitrile/alkyl methacrylate/butadiene terpolymers.

10. Polymers which are derived from unsaturated alcohols and amines or their acyl derivatives or acetals, such as polyvinyl alcohol, polyvinyl acetate, stearate, benzoate or maleate, polyvinylbutyral, polyallyl phthalate and polyallyl melamine.

11. Homopolymers and copolymers of cyclic ethers, such as polyalkylene glycols, polyethylene oxide, polypropylene oxide and copolymers thereof with bisglycidyl ethers.

12. Polyacetals, such as polyoxymethylene, and polyoxymethylenes containing comonomers, for example ethylene oxide.

13. Polyphenylene oxides and sulfides.

14. Polyurethanes which are derived from polyesters and polybutadienes with terminal hydroxyl groups on the one hand and aliphatic or aromatic polyisocyanates on the other hand, and intermediates thereof (polyisocyanates, polyols, prepolymers).

15. Polyamides and copolyamides which are derived from diamines and dicarboxylic acids and/or from aminocarboxylic acids or the corresponding lactams, such as polyamide 4, polyamide 6, polyamide 6,6, polyamide 6,10, polyamide 11, polyamide 12, poly-2,4,4,-trimethyl-hexamethylene-terephthalamide and poly-m-phenylene-isophthalamide, and copolymers thereof with polyethers, for example with polyethylene glycol, polypropylene glycol or polytetramethylene glycol.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-bis(4-hydroxyphenyl)propane]-terephthalate and polyhydroxybenzoates, and block polyether-esters which are derived from polyethers with hydroxyl end groups, dialcohols and dicarboxylic acids.

18. Polycarbonates.

19. Polysulfones and polyether-sulfones.

20. Crosslinked polymers which are derived from aldehydes on the one hand and phenols, urea and melamine on the other hand, such as phenol/formaldehyde, urea/formaldehyde and melamine formaldehyde resins.

21. Drying and non-drying alkyd resins.

22. Unsaturated polyester resins which are derived from copolyesters of saturated and unsaturated dicarboxylic acids with polyhydric alcohols, and vinyl compounds as crosslinking agents, and also the halogen-containing, slow-burning modifications thereof.

23. Crosslinkable acrylic resins which are derived from substituted acrylates, for example from epoxy acrylates, urethane-acrylates or polyester acrylates.

24. Alkyd resins, polyester resins and acrylate resins crosslinked with melamine resins, urea resins, polyisocyanates or epoxide resins.

25. Crosslinked epoxide resins which are derived from polyepoxides.

26. Natural polymers, such as cellulose, natural rubber, gelatine and polymer-analogous chemically modified derivatives thereof, such as cellulose acetates, propionates and butyrates and the cellulose ethers, such as methylcellulose.

Stabilisation of surface-coating resins, such as alkyd, acrylic and polyester resins, is of particular importance, especially in the use of these resins for acid-catalysed stoving varnishes.

The stabilisers according to the invention are added to the polymers in a concentration of 0.01 to 4% by weight, based on the material to be stabilised. Preferably, 0.1 to 2% by weight of the compounds, based on the material to be stabilised, is incorporated into this material.

The compounds can be incorporated before, during or after the polymerisation, for example by mixing them, if appropriate with other additives, into the melt by methods customary in the art, before or during shaping. In the case of varnishes, the compounds are preferably added to the solution of the varnish before its application.

The stabilisers can also be added in the form of a master batch, which contains these compounds in, for example, a concentration of 2.5 to 25% by weight, to the polymers to to be stabilised.

Besides the compounds of the formula I, other known stabilisers can also additionally be added to the polymers. These can be, for example, antioxidants, light stabilisers or metal deactivators, or costabilisers, for example those of the phosphite type. Other additives customary in plastics technology, for example flameproofing agents, antistatics, plasticisers, lubricants, glueing agents, pigments, reinforcing agents or fillers, can furthermore be added.

If known stabilisers are also used, synergistic effects may occur, which is frequently the case if other light stabilisers or organic phosphites are also used. The additional use of antioxidants is of particular importance in the stabilisation of polyolefins.

The invention thus also relates to the organic polymers which have been stabilised by addition of 0.1 to 4% by weight of a compound of the formula I and, if appropriate, may also contain other known and customary additives. The plastics thus stabilised can be used in the most diverse form, for example as films, fibres, small tapes, profiles or, in particular, as binders for varnishes.

The preparation and use of the compounds according to the invention is described in more detail in the examples which follow. In these examples, parts and percentages are by weight. The temperatures are given in degrees Centigrade.

In these examples, the formula

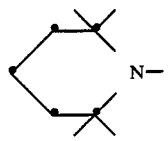

designates a 2,2,6,6-tetramethylpiperidine radical.

EXAMPLE 1

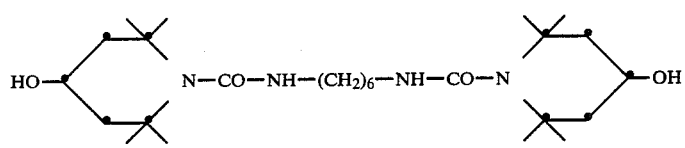

A solution of 16.8 g (0.1 mol) of hexamethylene diisocyanate in 50 ml of tetrahydrofuran is regularly added dropwise to a solution of 31.4 g (0.2 mol) of 4-hydroxy-2,2,6,6-tetramethylpiperidine in 300 ml of anhydrous tetrahydrafuran at 22°–25° C. in the course of 7 hours, while stirring. Stirring is then continued at room temperature overnight, whereupon a thick, white suspension of the reaction product precipitated forms. The reaction product is filtered off, washed thoroughly with cold tetrahydrofuran, filtered off with powerful suction and dried under a high vacuum at room temperature.

The dicarbamyl compound thus obtained is analytically pure and has a melting point of 145°–146°.
The $^1$H-NMR spectrum (CDCl$_3$) agrees well with the given structure.
C$_2$H$_{50}$N$_4$O$_4$ (482.7) Calculated: C 64.69 H 10.44 N 11.61%. Found: C 64.5 N 10.6 N 11.8%.
The compounds listed in Table 1 are prepared in a similar manner, from a polyalkylpiperidine and a diisocyanate:
TABLE 1
| Compound No. | Formula | Melting point |
|---|---|---|
| 1 | 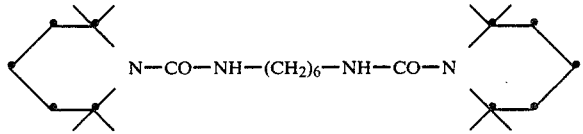 | 132–133° |
| 2 | 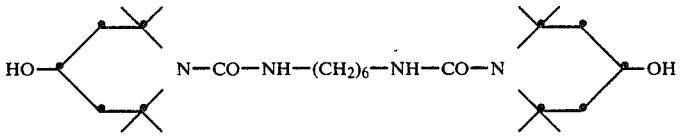 | 145–146° |
| 3 | 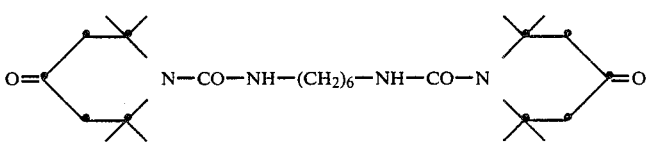 | 124–125.5° |
| 4 | 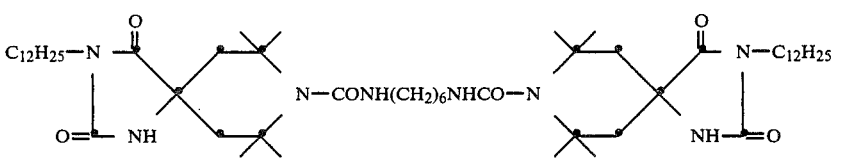 | 119–120° |
| 5 | 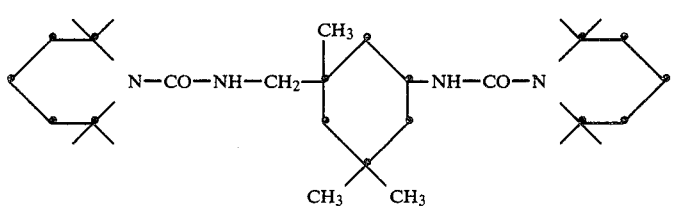 | 120.5–121° |
| 6 | 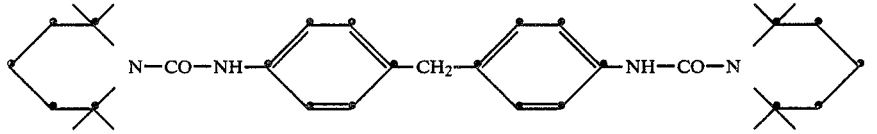 | 124.5–126° |
| 7 | 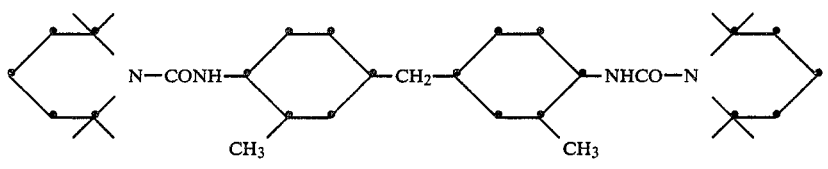 | 110–114° |
| 8 | 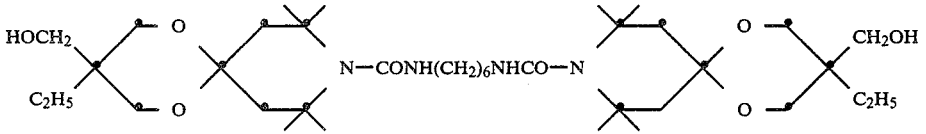 | 113–115° |

TABLE 1-continued

| Compound No. | Formula | Melting point |
|---|---|---|
| 9 | (structure with (CH$_2$)$_{11}$ bridges, piperidine rings linked by N—CONH(CH$_2$)$_6$NHCO—N, with HN and NH substituents) | 172–175° |
| 10 | (structure with (CH$_2$)$_{11}$ bridges, piperidine rings linked by N—CONH(CH$_2$)$_6$NHCO—N, with C$_6$H$_{13}$—N substituents) | 128–131° |
| 11 | (structure with phenyl-COO-piperidine-N—CONH-tolylene-NHCO-N-piperidine-OOC-phenyl) | 95–98° |
| 12 | RO—(piperidine)—N—CONH—(dimethyl-substituted cyclohexylene with CH$_3$ and CH$_3$/CH$_3$)—NHCO—N—(piperidine)—OR; R = HN—(piperidine)—OOC—(CH$_2$)$_8$—CO— | ~86° (amorphous) |
| 13 | RO—(piperidine)—N—CONH—CH$_2$—C(CH$_3$)$_2$—CH$_2$—CH(CH$_3$)—CH$_2$CH$_2$—NHCO—N—(piperidine)—OR | ~60° (amorphous) |

EXAMPLE 2

100 parts of polypropylene powder (Moplen, fibre grade, Montedison) are homogenised with 0.2 part of octadecyl β-(3,5-di-tert.-butyl-4-hydroxyphenyl)-propionate, 0.1 part of calcium stearate and 0.25 part of a stabiliser from the following Table 1 for 10 minutes in a Brabender plastograph at 200°. The mass thus obtained is removed from the kneader as rapidly as possible and pressed to a 2–3 mm thick sheet in a toggle press. A piece of the resulting crude moulding is cut out and pressed between two high-gloss hard aluminium foils with a hydraulic laboratory press at 260° for 6 minutes to give a 0.1 mm thick film, which is immediately chilled in cold water. Sections of this film are now stamped out and exposed in a Xenotest 1200. These test pieces are removed from the exposure apparatus at regular intervals of time and their carbonyl content is tested in a IR spectrophotometer. The increase in carbonyl extinction at 5.85 μm during the exposure is a measure of the photooxidative degradation of the polymer (cf. L. Balaban et al., J. Polymer Sci, Part C; 22 (1969), 1059–1071), and experience shows that this is associated with a deterioration in the mechanical properties of the polymer. The time taken for the carbonyl extinction to reach about 0.3, at which the comparison film is brittle, is a measure of the stabilising action.

| Stabiliser | Exposure time in hours |
|---|---|
| none | 900 |
| Compound No. 8 | >3420 |
| Compound No. 10 | >3420 |
| Compound No. 11 | 2300 |

What is claimed is:

1. A compound of the formula I

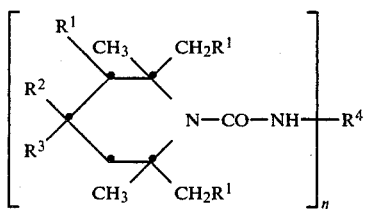

in which n is 2 or 3, $R^1$ is hydrogen, $R^2$ is —OH, —OR$^5$, —CH$_2$COOR$^6$, —CH$_2$CN, —N(R$^7$)—CO—R$^8$, —O—CO—R$^9$, —N(R$^7$)—CO—O—R$^{10}$, or —O—CO—N(R$^7$)$_2$ and $R^3$ is hydrogen, or $R^2$ and $R^3$ together are O=, 10 or a group of the formula II, III, IV, or V

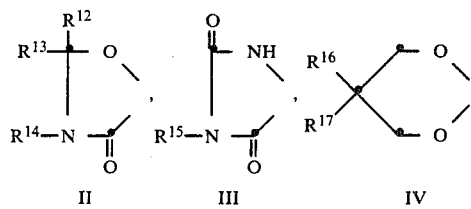

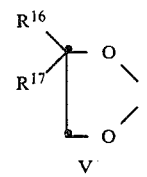

and, if n is 2, $R^4$ is $C_2$-$C_{12}$-alkylene, phenylene, naphthylene, tolylene or a group of the formula

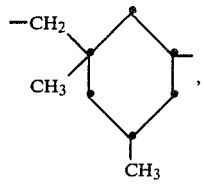

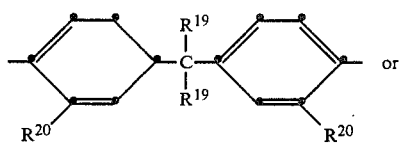

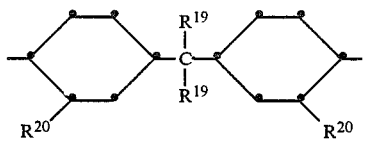

in which $R^{19}$ is hydrogen, methyl or ethyl and $R^{20}$ is hydrogen or methyl, and, if n is 3, $R^4$ is a group of the formula

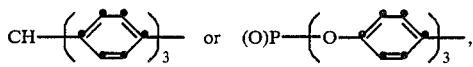

and $R^5$ is $C_1$-$C_{12}$-alkyl, $C_3$-$C_5$-alkenyl or benzyl, $R^6$ is $C_1$-$C_4$-alkyl or cyclohexyl, $R^7$ is $C_1$-$C_{12}$-alkyl, cyclohexyl, allyl or phenyl, $R^8$ and $R^9$ are $C_1$-$C_{12}$-alkyl, $C_2$-$C_3$-alkenyl, phenyl, benzyl or cyclohexyl, $R^{10}$ is $C_1$-$C_{12}$-alkyl or phenyl, $R^{12}$ is hydrogen, $C_1$-$C_{12}$-alkyl, $C_5$-$C_8$-cycloalkyl or benzyl and $R^{13}$ is $C_1$-$C_{12}$-alkyl, $C_5$-$C_8$-cycloalkyl or phenyl, or $R^{12}$ and $R^{13}$, together with the C atom to which they are bonded, are a $C_6$-$C_{14}$-cycloalkane or alkylcycloalkane ring, $R^{14}$ is hydrogen, $C_1$-$C_{12}$-alkyl, $C_3$-$C_5$-alkenyl, $C_5$-$C_8$-cycloalkyl, $C_2$-$C_4$-hydroxyalkyl, $C_2$-$C_{10}$-alkanoyl, benzoyl, $C_7$-$C_{12}$-phenylalkyl or a group R—NH—CO—, in which R is $C_1$-$C_8$-alkyl or phenyl, $R^{15}$ is hydrogen, $C_1$-$C_{18}$-alkyl, $C_3$-$C_5$-alkenyl, $C_2$-$C_4$-hydroxyalkyl, $C_5$-$C_8$-cycloalkyl, $C_1$-$C_{12}$-phenylalkyl or glycidyl, $R^{16}$ is hydrogen or $C_1$-$C_4$-alkyl and $R^{17}$ is hydrogen, methyl, ethyl or hydroxymethyl.

2. The compound

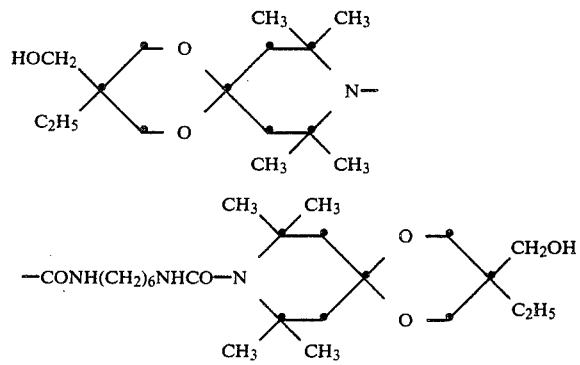

according to claim 1.

3. The compound

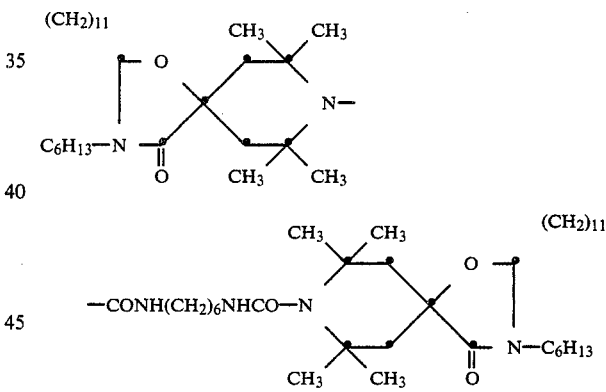

according to claim 1.

4. The compound

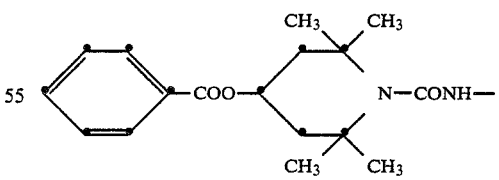

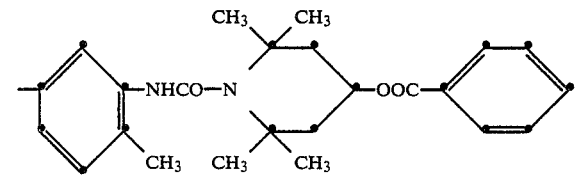

according to claim 1.

* * * * *